(12) United States Patent
Hopkinson, III et al.

(10) Patent No.: US 10,036,733 B2
(45) Date of Patent: Jul. 31, 2018

(54) HARDNESS VERIFICATION UTILIZING ULTRASONIC VELOCITIES

(71) Applicants: ZF Friedrichshafen AG, Friedrichshafen (DE); MAGNACHEK, Madison Heights, MI (US)

(72) Inventors: Harold Hopkinson, III, Farmington Hills, MI (US); Wally Lawrence, Madison Heights, MI (US); Eric Holmes, Northville, MI (US); Joel Lautermilch, Northville, MI (US); Tracy Holmes, Northville, MI (US)

(73) Assignees: ZF Friedrichshafen AG, Friedrichshafen (DE); Magnachek, Madison Heights, MI (US)

( * ) Notice: Subject to any disclaimer, the term of this patent is extended or adjusted under 35 U.S.C. 154(b) by 116 days.

(21) Appl. No.: 14/684,763

(22) Filed: Apr. 13, 2015

(65) Prior Publication Data
US 2016/0299107 A1   Oct. 13, 2016

(51) Int. Cl.
*G01N 29/07*   (2006.01)
*G01B 17/02*   (2006.01)
*G01N 29/22*   (2006.01)

(52) U.S. Cl.
CPC ............ *G01N 29/07* (2013.01); *G01B 17/02* (2013.01); *G01N 29/226* (2013.01); *G01N 2291/011* (2013.01); *G01N 2291/02827* (2013.01); *G01N 2291/044* (2013.01)

(58) Field of Classification Search
CPC ........ G01N 29/07; G01N 29/226; G01N 3/40; G01B 17/02
See application file for complete search history.

(56) References Cited

U.S. PATENT DOCUMENTS

| | | | | |
|---|---|---|---|---|
| 3,858,438 A * | 1/1975 | Neumann | ............... | G01B 17/02 73/615 |
| 4,574,637 A * | 3/1986 | Adler | ..................... | G01N 29/00 73/599 |
| 4,702,110 A * | 10/1987 | Holt | ....................... | G01N 29/07 73/573 |
| 4,914,952 A * | 4/1990 | Miyajima | .......... | G01N 29/0645 73/598 |
| 5,095,465 A * | 3/1992 | Stokoe, II | ............ | G01N 29/041 367/14 |

(Continued)

*Primary Examiner* — Helen Kwok
(74) *Attorney, Agent, or Firm* — Davis & Bujold PLLC; Michael J. Bujold

(57) ABSTRACT

A method and system for determining a hardness of a component to be tested by utilizing an ultrasonic meter. The method and system both comprise selecting a component to be tested which has a longitudinal axis; positioning a probe of the ultrasonic meter for emitting a signal from an emitter of the probe into an end surface of the component to be tested and along the longitudinal axis of the component; emitting the signal from the emitter of the probe into the first surface of the component to be tested; passing the emitted signal through the component to be tested; reflecting the emitted signal via an opposed second surface of the component to be tested back toward a detector of the probe; detecting the reflected signal via the detector of the probe; and determining a hardness of the component to be tested based upon a velocity of the emitted signal.

13 Claims, 5 Drawing Sheets

(56) References Cited

U.S. PATENT DOCUMENTS

| | | | | | |
|---|---|---|---|---|---|
| 5,216,921 | A * | 6/1993 | Tsuboi | ................ | G01N 29/12 702/39 |
| 5,349,860 | A * | 9/1994 | Nakano | ................ | G01N 29/07 702/171 |
| 5,533,411 | A * | 7/1996 | Koiwa | ................ | G01N 29/07 73/598 |
| 5,557,047 | A * | 9/1996 | Koide | ................ | G01H 5/00 73/24.06 |
| 5,559,292 | A * | 9/1996 | Hull | ................ | G01N 29/02 73/597 |
| 5,635,644 | A * | 6/1997 | Ishikawa | ................ | G01B 17/025 73/614 |
| 5,672,828 | A * | 9/1997 | Allan | ................ | G01N 29/07 73/159 |
| 5,970,434 | A * | 10/1999 | Brophy | ................ | G01B 17/02 324/220 |
| 6,234,025 | B1 * | 5/2001 | Gieske | ................ | G01N 29/221 73/629 |
| 6,276,209 | B1 * | 8/2001 | Schafer | ................ | G01N 29/07 73/597 |
| 6,494,840 | B1 * | 12/2002 | Mak | ................ | A61B 8/0858 600/443 |
| 6,584,847 | B1 * | 7/2003 | Hirose | ................ | G01B 17/00 73/579 |
| 7,171,854 | B2 * | 2/2007 | Nagashima | ................ | G01N 29/221 73/612 |
| 2002/0100326 | A1 * | 8/2002 | Stein | ................ | G01N 29/0609 73/597 |
| 2003/0230140 | A1 * | 12/2003 | Eccardt | ................ | G01N 29/07 73/159 |
| 2006/0207329 | A1 * | 9/2006 | Page | ................ | G01N 3/40 73/597 |
| 2006/0219012 | A1 * | 10/2006 | Huang | ................ | G01N 29/07 73/597 |
| 2007/0095139 | A1 * | 5/2007 | Hara | ................ | G01N 29/07 73/628 |
| 2008/0022773 | A1 * | 1/2008 | McKenna | ................ | G01H 5/00 73/597 |
| 2008/0098818 | A1 * | 5/2008 | Fernald | ................ | G01F 1/7082 73/622 |
| 2009/0078046 | A1 * | 3/2009 | Coghill | ................ | G01N 29/07 73/597 |
| 2009/0229364 | A1 * | 9/2009 | Gysling | ................ | G01B 17/02 73/623 |
| 2012/0055251 | A1 * | 3/2012 | Kono | ................ | G01B 17/02 73/597 |
| 2013/0231884 | A1 * | 9/2013 | Yanagihara | ................ | G01N 29/07 702/97 |
| 2014/0208852 | A1 * | 7/2014 | Instanes | ................ | G01B 17/02 73/594 |
| 2014/0260638 | A1 * | 9/2014 | Hood | ................ | G01N 29/14 73/647 |
| 2015/0233806 | A1 * | 8/2015 | More | ................ | G01N 3/42 73/85 |

* cited by examiner

HARDNESS VERIFICATION UTILIZING ULTRASONIC VELOCITIES

FIELD OF THE INVENTION

The present invention relates to a non-destructive method and a system for measuring the hardness of a desired component, such as a component utilized within a vehicle.

BACKGROUND OF THE INVENTION

As is well known in the art, a variety of components are subject to a heat treatment process, during a manufacturing process, in order to modify/alter the hardness of the component prior to use. That is, such components are typically heat treated in order to enhance the strength and/or toughness of the metal from which the component is manufactured. In addition, for some applications, only a selected portion or section of the component, e.g., such as a case hardened outer surface, may be heat treated while a remaining portion or section of the component may not be heat treated.

A typical conventional procedure for checking the hardness of a component is to first cut the component in half and thereafter make a mark or an indentation in the exposed surface of the component. The curvature or diameter of the indentation is then measured and the hardness of the component is then calculated by utilizing either a Vickers scale or Brinell scale. As is to be appreciated from the above described conventional procedure, since the component must be cut in half in order to determine its hardness of the component, the component is essentially destroyed and then becomes useless following a determination of its hardness.

Ball studs, for example, which are used in steering and/or suspension mechanisms for automobiles, are typically heat-treated during the manufacturing process. However, it is difficult to determine, in a non destructive manner, whether or not each one of the heat-treated components has been properly heat-treated so that such heat treated components have the desired hardness. In addition, the problem of measuring the hardness of a desired component is compounded when there is the existence of a case hardened outer surface on the component of interest.

Moreover, on a few occasions, it may become necessary to "recall" a defective component(s), following installation thereof. In such a situation, it is desirable to have a way or process which allows a manufacturer to readily examine and determine which components, following installation thereof, are acceptable and do not require replacement and which are defective and must replaced.

SUMMARY OF THE INVENTION

Wherefore, it is an object of the present invention to overcome the above mentioned shortcomings and drawbacks associated with the prior art by providing a system and a method which facilitates the detection of the amount of heat treatment provided to a component.

Another object of the present invention is to provide a method and a system which allows the user to quickly and readily determine the hardness of a component, following heat-treated thereof, for determining whether or not the component is adequately treated.

A further object of the present invention is to facilitate determining, in a nondestructive manner, the hardness of the component, at any particular point, during the manufacturing process, as well as to facilitate determining the hardness of the component, following manufacture thereof and even following installation of the component.

Yet another object of the present invention is to facilitate determining the hardness of a component's internal hardness, when a case or surface hardness of the component generally inhibits and/or prevents measurement of the hardness of the component by another technique or method.

Still a further object of the present invention is to facilitate measuring/determining the hardness of a component, in a nondestructive manner following installation thereof, when it is not convenient or otherwise easy to disassemble the installed component in order to measure/determine its hardness.

A further object of the present invention is to provide a nondestructive method and a system which emits a desired signal, e.g., an ultrasonic, an eddy current, etc., which can be utilized to quickly and easily determine the hardness of a desired component.

The present invention also relates to a method of determining a hardness of a component to be tested by utilizing an ultrasonic meter, the method comprising the steps of: selecting a component to be tested which has a longitudinal axis; positioning a probe of the ultrasonic meter for emitting a signal from an emitter of the probe into a first end surface of the component to be tested; emitting the signal from the emitter of the probe into the first surface of the component to be tested and along the longitudinal axis of the component and passing the emitted signal through the component to be tested; reflecting the emitted signal, via an opposed second surface of the component to be tested, back toward a detector of the probe; detecting the reflected signal via the detector of the probe; and determining a hardness of the component to be tested based upon a velocity of the emitted signal through the component to be tested The present invention also relates to a system for determining a hardness of a component to be tested which comprises an ultrasonic meter, the system comprising: a component to be tested which has a longitudinal axis; the ultrasonic meter having a probe for emitting a signal from an emitter of the probe into a first end surface of the component to be tested; the emitter of the probe being located for emitting the signal into the first surface of the component to be tested so that the emitted signal passes through the component to be tested and along the longitudinal axis of the component and is reflected by an opposed second surface of the component to be tested back toward a detector of the probe; the detector of the probe detects the reflected signal, and a hardness of the component to be tested is determined based upon a velocity of the emitted signal passing through the component to be tested.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. The invention will now be described, by way of example, with reference to the accompanying drawings in which.

It should be understood that the drawings are not necessarily to scale and that the disclosed embodiments are sometimes illustrated diagrammatically and in partial views. In certain instances, details which are not necessary for an understanding of this disclosure or which render other details difficult to perceive may have been omitted. It should be understood, of course, that this disclosure is not limited to the particular embodiments illustrated herein.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
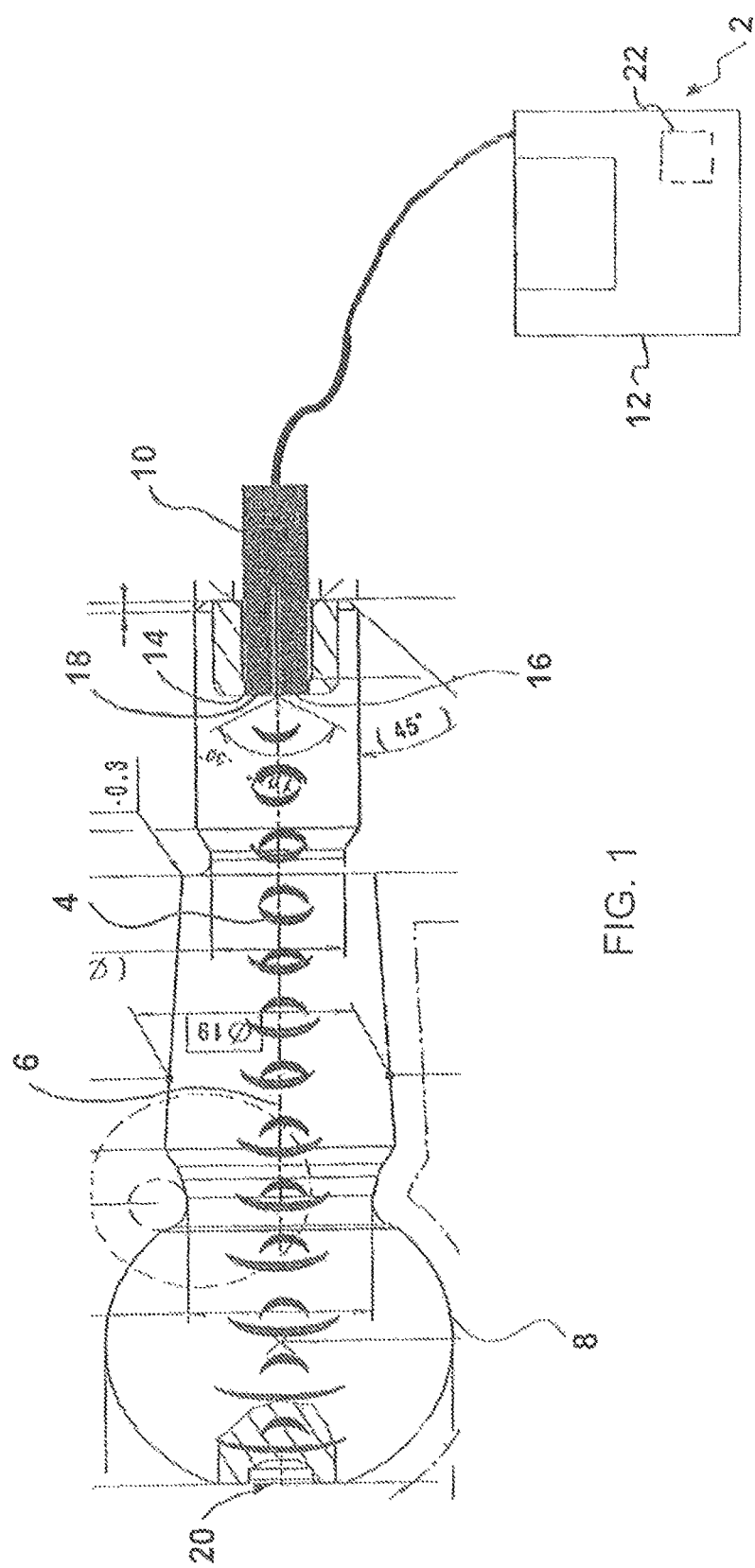
FIG. 1 is a diagrammatic drawing showing the basic components of the method and the system for practicing the present invention.

Turning now to FIG. 1, a brief description concerning the various components of the present invention will now be briefly discussed. As can be seen in this figure, a conventional thickness (ultrasonic) meter 2 is utilized to send a signal or wave 4 along a longitudinal length or axis 6 of a component 8 to be tested in order to determine the hardness of that component 8. The speed at which this signal or wave 4 travels, e.g., its velocity, is measured and the inventors have discovered that the speed/velocity of the signal or wave 4 through the component 8 to be tested varies proportionally to the hardness of the component. That is, for component 8 which has a (relatively) lower hardness, the signal or wave 4 travels at a relatively faster or higher speed through that component 8 in comparison to a component 8 which has a (relatively) higher hardness in which the emitted signal or wave 4 travels at a relatively slower or lower speed through that component 8.

As generally shown, the thickness (ultrasonic) meter 2 comprises an easily manipulatable and portable probe 10 which is electrically connected or coupled, by conventional cabling or wiring, to a main console 12 of the thickness (ultrasonic) meter 2. A leading end face 14 of the portable probe 10 is generally flat and supports both an emitter 16, for emitting a desired signal or wave 4, and a sensor/detector 18, for receiving, sensing and/or detecting a returned signal or wave 4. The emitter 16 is capable of emitting a desired ultrasonic signal, e.g., typically the signal has a wavelength in the range of 20-100 kHz for example, (possibly about 5 megahertz or so) while the sensor/detector 18 is capable of detecting a return signal or wave 4 within a similar frequency range. A suitable handheld thickness (ultrasonic) meter 2 for the practice of the present invention is, for example, model number Epoch III manufactured by Olympus Panametrics.

As shown in FIG. 1, the component 8 to be tested in this example is a conventional heat-treated ball stud. It is to be appreciated that a variety of other automobile components and/or other heat treated components in other industries may be tested, in place of the ball stud, in order to facilitate determining the hardness of such component 8. During use, the planar or flat end face 14 of the portable probe 10 is generally placed in abutting engagement against a flat or planar surface of the component 8 to be tested. That is, the mating surfaces of the portable probe 10 and the component 8 to be tested are arranged substantially parallel to one another so that the longitudinal axis 6 of the component 8 to be tested extends generally normal to the planar end face 14 of the portable probe 10. Once the portable probe 10 is properly located in this orientation or position, the thickness (ultrasonic) meter 2 is then energized so that a desired signal or wave 4 (e.g., 5 megahertz or example) is emitted by the emitter 16 and transmitted directly into the abutting flat or planar surface of the component 8 to be tested. It is conceivable that the planar end face 14 may be spaced a very small distance away from the flat or planar surface of the component 8 to be tested.

As diagrammatically shown in FIG. 1, the emitted signal or wave 4 initially travels along the longitudinal axis 6 of the component 8 to be tested until the emitted signal or wave 4 eventually reaches an opposed end surface 20 of the component 8 to be tested. Once the emitted signal or wave 4 reaches the opposite end surface 20 of the component 8 to be tested, the emitted signal or wave 4 is then reflected by that end surface 20 back toward the sensor/detector 18 of the portable probe 10. As soon as the reflected signal or wave 4 reaches the end face 14 of the portable probe 10, the sensor/detector 18 of the probe senses/detects the reflected signal or wave 4. An internal processor 22 utilizes this reflective signal or wave 4 to determine, in a conventional manner, the velocity of the emitted signal or wave 4 traveling through the component 8 to be tested, e.g, ball stud, from the emitter 16 to the opposite end surface 20 of the component 8 to be tested and returned back to and received by the sensor/detector 18. The internal processor 22 (only diagrammatically shown), located within the main console 12 of the thickness (ultrasonic) meter 2, will then utilize the time that it took the emitted signal or wave 4 to travel to and fro along the length of the component 8 to be tested, the overall length of the component 8 to be tested and the frequency of the emitted signal in order to determine a hardness of the component 8 to be tested, as will be discussed below in further detail.

Figure 2:
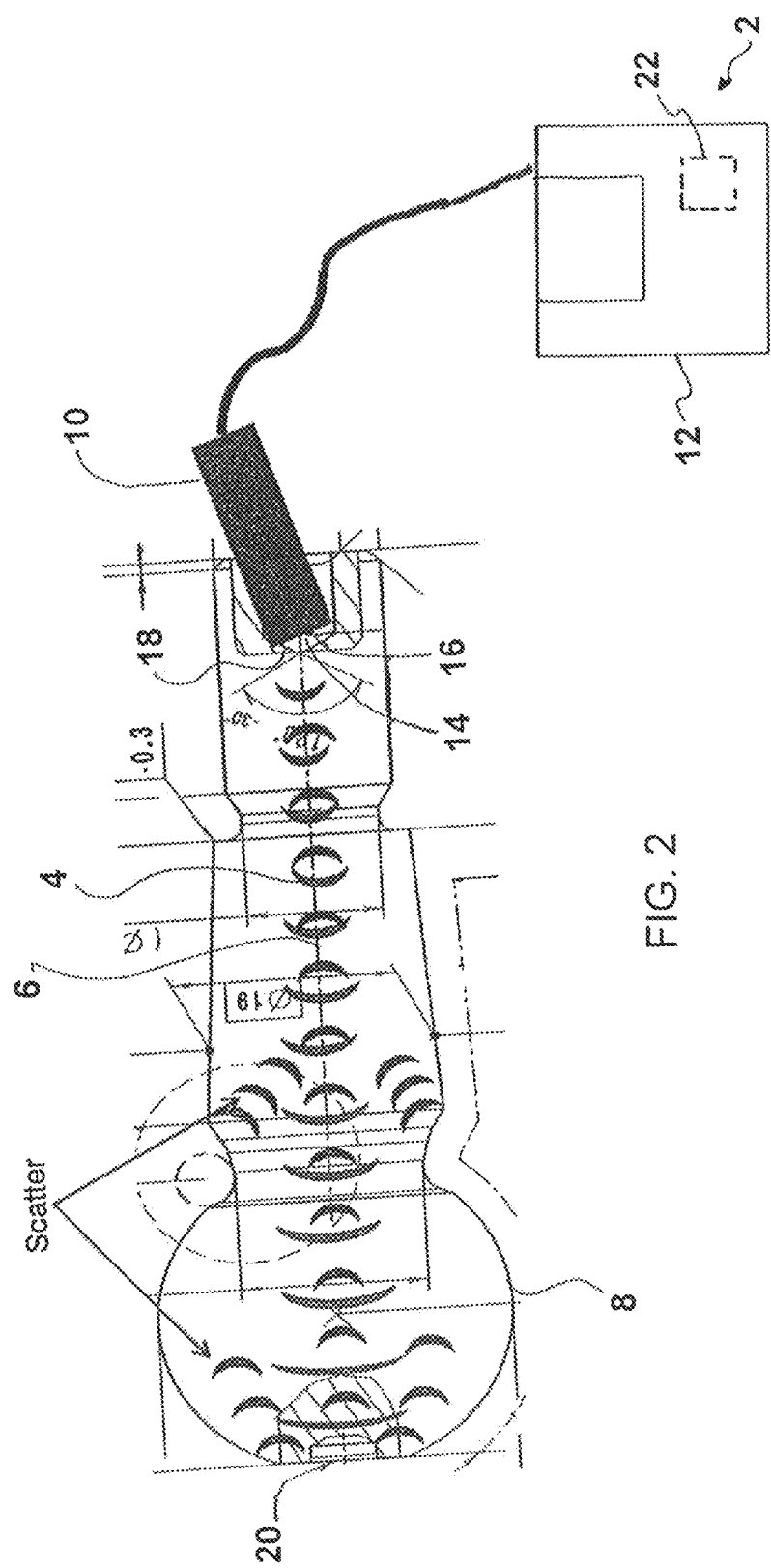
FIG. 2 is a diagrammatic view, similar to FIG. 1, showing a potential problem which may occur in the event that the emitted signal is not sent along the longitudinal axis of the component to be tested.
Figure 3:
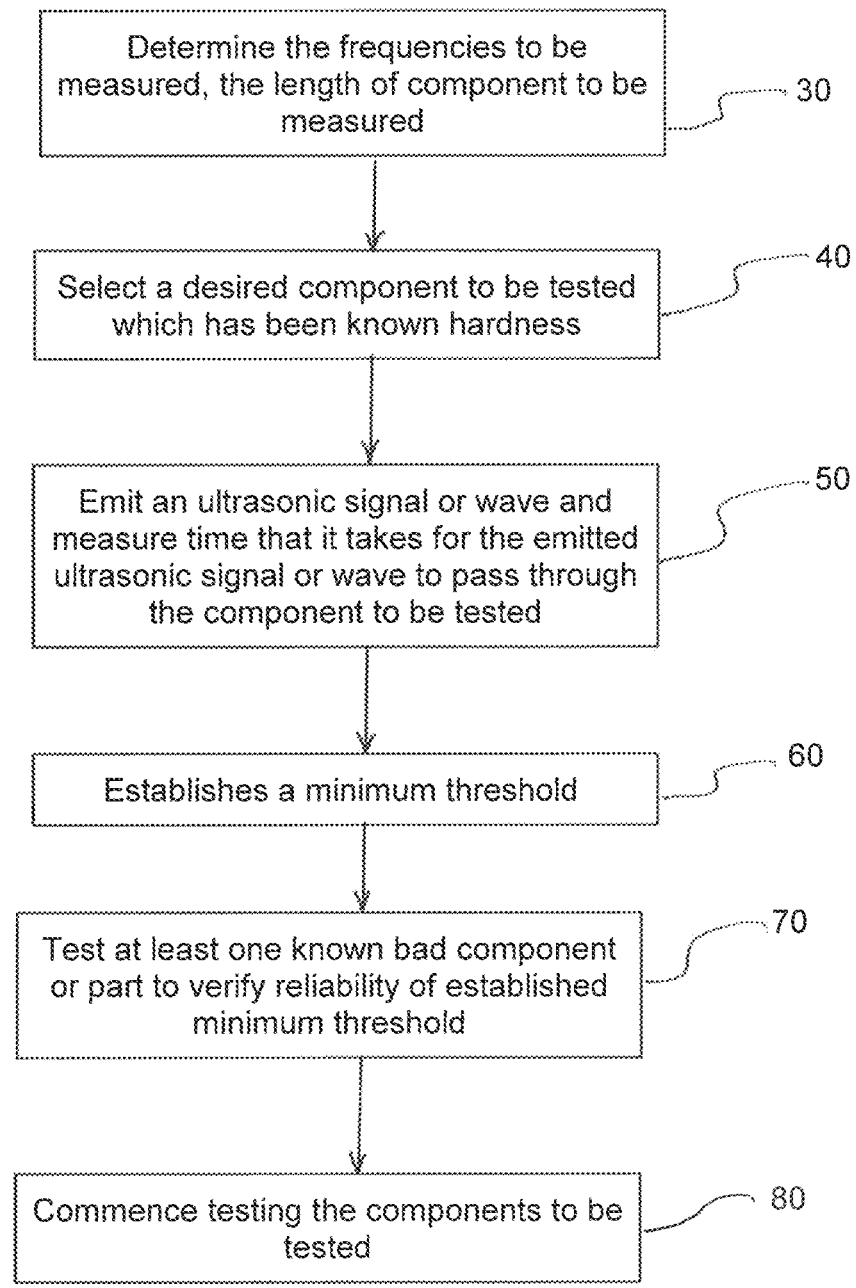
FIG. 3 is a diagrammatic flow diagram showing the method steps of the present invention.

With reference now to FIG. 2, one potential problem, associated with the method and the system of the present invention will now be briefly discussed. As diagrammatically shown in this Figure, in the event that the end face 14 of the portable probe 10 is not placed in an abutting relationship with the flat or planar surface of the component 8 to be tested, which lies normal to the longitudinal axis 6 of the component 8 to be tested, then the emitted signal or wave 4 may be emitted from the portable probe 10 at an angle relative to the longitudinal axis 6 of the component 8 to be tested, rather than parallel to and along the longitudinal axis 6 of the component 8 to be tested. In such instance, since the emitted signal or wave 4 is emitted at an angle relative to the longitudinal axis 6 of the component 8 to be tested, the emitted signal has a tendency to reflect or bounce off one or more side walls or surfaces of the component, 8 to be tested, thereby scattering or altering (e.g., increases or decreases) the time that it takes for the emitted signal or wave 4 to travel along the length of the component 8 to be tested, be reflected back by the opposite end surface 20 of the component 8 to be tested, and returned back to the sensor/detector 18, thereby skewing the obtained results as well as the determined velocity of the emitted signal or wave 4 to travel through the component 8 to be tested.

Preferably, the longitudinal axis 6 of the component 8 to be tested extends normal to the end face of the portable probe 10. When the probe 10 is arranged in such an orientation, this ensures that the emitted signal or wave 4 is emitted generally along the longitudinal axis 6 of the component 8 to be tested and thereby minimizes the possibility of the emitted signal or wave 4 reflecting, bouncing or scattering off one or more side walls or other surfaces of the component 8 to be tested. In addition, preferably the opposed end surface 20 of the component 8 to be tested is flat or otherwise capable of reflecting the emitted signal or wave 4 directly back along the longitudinal axis 6 of the component 8 to be tested to the sensor/detector 18 of the portable probe 10.

Figure 4:
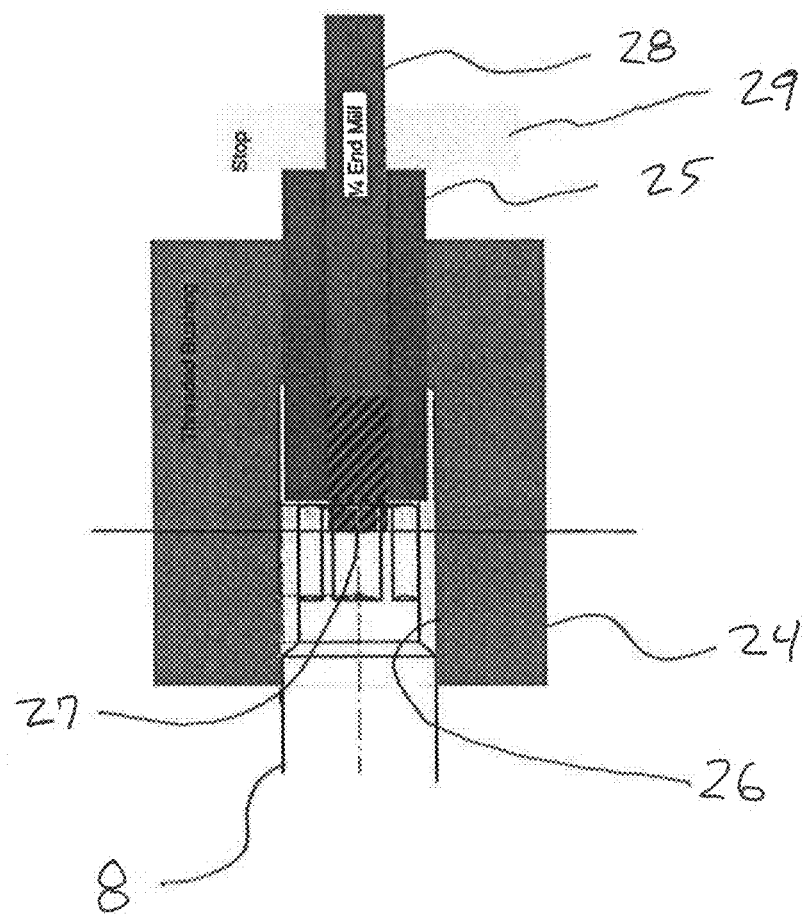
FIG. 4 is diagrammatic drawing showing a way to qualify a flat normal surface to the end of a ball stud, i.e., either with an external hex or an internal hex, so as to improve the measurement accuracy and avoid misalignment and/or poor readings.

FIG. 4 is diagram drawing showing one way to qualify a flat normal surface to the end of a ball stud so as to have a flat surface for engaging with the flat end face 14 of the portable probe 10 and thereby improve the measuring accuracy and avoid any to misalignment or poor readings when measuring the velocity of a component to be tested 8. That is, align a longitudinal axis of the probe 10 with the longitudinal axis 6 of the component 8 to be tested so that they are both coincident and concentric with one another.

As generally shown in FIG. 4, a threaded bushing 24 can be threaded to the first end of the component 8 to be tested, e.g., around an external hex in this embodiment. The threaded bushing 24 mates with an external thread and has an internal bore 26 which is sized to receive and closely accommodate a conventional milling bit 28 which has a flat face 27. The internal bore 26 is designed to receive and align the flat faced milling bit 28 so as to be concentric and coincidence with the longitudinal axis 6 of the component 8 to be tested. If necessary, a spacer sleeve 25 can be accommodated within the internal bore 26 to assist with aligning the flat faced milling bit 28 within the internal bore 26. The flat faced milling bit 28 is both rotatable and movable with respect to the spacer sleeve 25. Lastly, a stop member 29 can be utilized to limit the distance or amount that the flat faced milling bit 28 is permitted to extend into the internal bore 26 of the bushing 24 for machining a flat surface into the first end of the ball stud, enabling a repeatable length of measurement.

It is to be appreciated that the threaded bushing 24 can also be threaddly secured to the first end of the component 8 to be tested which has an internal hex, in a similar manner, in order to form a flat surface on the first end of the ball stud for mating with the flat end face 14 of the portable probe 10.

The system and the method, according to the president invention, is normally first calibrated by selecting a desired component 8 to be tested which has a first known hardness, and emitting a desired signal or wave 4, at a desired frequency, through that desired component 8 to be tested. If desired, a plurality of identical components which each have substantially identical hardnesses can be tested as a group to determine an average velocity for the desired signal or wave 4 traveling through the desired component 8 to be tested.

Preferably, the same signal or wave 4 may also be emitted, from the portable probe 10 of the thickness (ultrasonic) meter 2, through one or more additional components 8 to be tested which each have a second known hardness (e.g., typically a hardness which is slightly higher (or slightly lower) than the first known hardness). If desired, a plurality of identical components which each have substantially identical second known hardnesses can be tested to determine an average velocity of the desired signal or wave 4 through the components 8 to be tested which each have the second known hardness.

More preferably, the same signal or wave 4 is also emitted, from the portable probe 10 of the thickness (ultrasonic) meter 2, through one or more additional components 8 to be tested which has a third known hardness (e.g., typically slightly lower (or slightly higher) than the first known hardness). If desired, a plurality of identical components which each have substantially identical third known hardnesses can be tested to determine an average velocity of the desired signal or wave 4 through the components 8 to be tested which have the third known hardness.

Depending upon the accuracy desired, the above process can be repeated for a number of different components 8 to be tested which each have different, but known, slightly lower or slightly higher hardnesses than the first, the second and the third known hardnesses so as to determine an average velocity of the desired signal or wave 4 through the components 8 to be tested which have a variety of different, but known, hardnesses, All of this information can then be collected and utilized (e.g., plotted) to determine the hardness of other components 8 to be tested which have an unknown hardness.

Once all the foregoing information is collected and compiled, a desired minimum threshold velocity can be established. Once the minimum threshold velocity is established, then one or more components 8 to be tested, which each have a hardness which is currently unknown, can be tested and, based upon the velocity of the signal or wave 4 traveling through such component 8 to be tested, the hardness of the component 8 to be tested can be quickly, reliably and easily ascertained.

In summation, the normal practice or procedure, for a given part and material hardness, is as follows. This procedure includes determining, at step 30, the frequencies to be measured, the component or part to be tested (step 40), the length of parts to be measured, as well as a robust threshold (at step 60) which is to be established by determining acceptable or "good" parts or components from unacceptable or "bad" parts or components. The ultrasonic meter 2 is first used to measure at least one acceptable or "good" part or component, e.g., a ball stud, at step 50, and the method and the system is verified that the equipment is in calibration for the component 8 to be tested, e.g, a ball studs, normal material and length. The equipment is then used on at least one known bad component or part to verify the reliability of the established minimum threshold (step 70). Once the method and the system are qualified, an operator is then able to measure the desired parts or components 8 to be tested (step 80) to determine whether or not each one of these parts or components 8 to be tested are acceptable or "Okay" and thus can be further processed, used, installed, remain installed, etc., or are unacceptable or "Not Okay" for use, further processing, installation, replaced, etc., and thus should be rejected and recycled.

Figure 5:
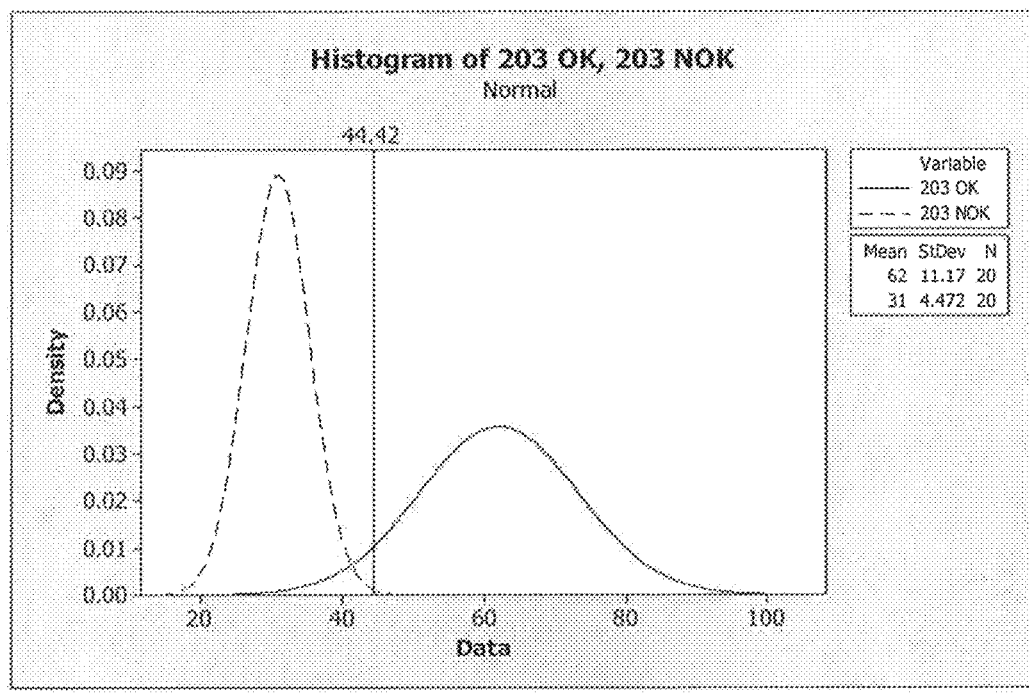
FIG. 5 is a graph displaying the results of 40 measurements of 20 components or parts which are known to be "good" parts and 20 components or parts which are known to be "bad" parts.

As shown in the graph depicted FIG. 5, the established minimum threshold is, in this example, 44.42. As generally shown in this figure, each component 8 to be tested which has a test value that is greater than or equal to the minimum threshold of 44.42 is indicated as having a suitable hardness and is accepted for subsequent processing, use, installation, etc. However, as also generally shown in this figure, each component 8 to be tested which has a test value that is less than the minimum threshold of 44.42 is indicated as having an unsuitable or unacceptable hardness and is rejected, e.g., such component is not processed further, used, installed, replaced, etc. In example shown in this figure, a total of 40 measurements were made on 20 parts or components which were each previously known to be "good" parts or components and also made on 20 parts or components which were previously known to be "bad" parts or components. Based upon data of this example, it was determined that 99.86% of the "bad" parts would be caught/rejected by the method and the system according to the present invention while approximate 2-5% of the acceptable or good parts or components may be falsely rejecting based on 2 sigma of good parts (39.66). In this example, good parts were parts with a core hardness of ~520 Vickers, in comparison to bad parts which had a core hardness of ~650-700 Vickers.

By use of the present method, one can easily verify by the measurement, based upon whether the reading is outside the established threshold, if a component is a good part or a bad part. It is to be appreciated that the acceptance/rejection rate can be readily modified by varying the minimum threshold value.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a !imitative sense.

Wherefore, we claim:

1. A method of determining a hardness of a component to be tested by utilizing an ultrasonic meter, the method comprising the steps of:
    selecting an elongate component to be tested which has a central longitudinal axis and a first end surface that is perpendicular to the longitudinal axis;
    positioning a probe of the ultrasonic meter relative to the component such that the probe is concentric with the longitudinal axis of the component and a signal from an emitter of the probe is emitted along the longitudinal axis and through the first end surface into the component to be tested and travels along the longitudinal axis;
    emitting the signal from the emitter of the probe along the longitudinal axis and through the first end surface into the component to be tested, and the emitted signal passing through the component to be tested along the longitudinal axis;
    reflecting the emitted signal off an opposed second end surface of the component to be tested directly back along the longitudinal axis through the component to be tested toward a detector of the probe, and the probe being positioned relative to the component such that the emitted signal is reflected directly back along the longitudinal axis through the first end surface to the detector of the probe;
    detecting the reflected emitted signal via the detector of the probe; and
    determining a hardness of the component to be tested based upon a velocity of the emitted signal through the component to be tested.

2. The method of determining the hardness of the component to be tested according to claim 1, further comprising the steps of locating both the emitter and the detector closely adjacent one another in an end face of the probe, and the end face being perpendicular to a longitudinal axis of the probe.

3. The method of determining the hardness of the component to be tested according to claim 2, further comprising the steps of positioning the probe so that the longitudinal axis of the probe is coincident with the longitudinal axis of the component and the end face of the probe abuts the first end surface of the component to be tested.

4. The method of determining the hardness of the component to be tested according to claim 1, further comprising the steps of:
    determining a minimum threshold value;
    accepting the component to be tested which have a value above the minimum threshold value; and
    rejecting the component to be tested which have a value below the minimum threshold value.

5. The method of determining the hardness of the component to be tested according to claim 1, further comprising the steps of:
    determining a minimum threshold value;
    accepting the component to be tested which have a value equal to or above the minimum threshold value; and
    rejecting the component to be tested which have a value below the minimum threshold value.

6. The method of determining the hardness of the component to be tested according to claim 4, further comprising the step of determining the minimum threshold value by testing at least one component to be tested which has a known hardness.

7. The method of determining the hardness of the component to be tested according to claim 4, further comprising the step of verifying a reliability of the minimum threshold value by testing at least one component to be tested which has a known hardness less than the minimum threshold value.

8. A system for determining a hardness of a component to be tested which comprises an ultrasonic meter, the system comprising:
    an elongate component to be tested which has a central longitudinal axis and a first end surface that is perpendicular to the longitudinal axis of the component;
    the ultrasonic meter having a probe comprising a longitudinal axis, the probe being aligned with the component to be tested such that the probe is concentric with the longitudinal axis of the component and the longitudinal axis of the probe is coaxial to the longitudinal axis of the component to be tested, and the probe emitting a signal from an emitter of the probe along the longitudinal axis of the probe and through the first end surface of the component to be tested;
    the emitter of the probe being located for emitting the signal along the longitudinal axis of the probe and through the first end surface into the component to be tested so that the emitted signal passes through the component to be tested and along the longitudinal axis of the component and is reflected by an opposed second end surface of the component to be tested back through the component to be tested toward a detector of the probe along the longitudinal axis of the component to be tested;

the detector of the probe detects the reflected signal, and a hardness of the component to be tested is determined based upon a velocity of the emitted signal passing through the component to be tested and along the longitudinal axis of the component to be tested.

9. A method of determining a hardness of a ball joint following heat treatment during manufacture thereof utilizing an ultrasonic meter to ascertain acceptability of the bail joint, the method comprising:

selecting at least first and second ball joints having longitudinal axes that extend from planar surfaces on first axial ends of the first and the second ball joints to fiat surfaces on axially opposite ball ends of the first and the second ball joints, and the first ball joint having a known hardness, and the second ball joint having a known hardness that is different than the known hardness of the first ball joint, and the planar surfaces and the flat surfaces of the first and the second ball joints, respectively, being perpendicular to the longitudinal axes of the respective first and the second ball joints;

positioning a probe of the ultrasonic meter relative to the first ball joint such that the probe is concentric with the longitudinal axis of the first ball joint and a flat axially leading surface of the probe is parallel to and mates with the planar surface of the first ball joint, and the leading surface of the probe supporting an emitter and a detector;

emitting first ultrasonic signals from the emitter of the probe through the planar surface of the first ball joint, the first ultrasonic signals passing along the longitudinal axis of the first ball joint and being reflected by the flat surface of the first ball joint directly back along the longitudinal axis thereof to the detector of the probe;

detecting the reflected first ultrasonic signals with the detector of the probe;

determining a velocity of the first ultrasonic signals through the first ball joint;

positioning the probe of the ultrasonic meter relative to the second ball joint such that the probe is concentric with the longitudinal axis of the second ball joint and the flat axially leading surface of the probe is parallel to and mates with the planar surface of the second ball joint;

emitting second ultrasonic signals from the emitter of the probe through the planar surface of the second ball joint, and the second ultrasonic signals passing along the longitudinal axis of the second ball joint and being reflected by the fiat surface of the second ball joint directly back along the longitudinal axis thereof to the detector of the probe;

detecting the reflected second ultrasonic signals with the detector of the probe;

determining a velocity of the second ultrasonic signals through the second ball joint;

selecting a third ball joint having a longitudinal axis that extends from a planar surface on a first axial end of the third ball joint to a flat surface on an axially opposite ball end of the third ball joint, and the third ball joint having an unknown hardness, and the planar surface and the flat surface of the third ball joint being perpendicular to the longitudinal axis of the third ball joint;

positioning the probe of the ultrasonic meter relative to the third ball joint such that the probe is concentric with the longitudinal axis of the third ball joint and the flat axially leading surface of the probe is parallel to and mates with the planar surface of the third ball joint;

emitting third ultrasonic signals from the emitter of the probe through the planar surface of the third ball joint, the third ultrasonic signals passing along the longitudinal axis of the third ball joint and being reflected by the flat surface of the third ball joint directly back along the longitudinal axis of the third ball joint to the detector of the probe;

detecting the reflected third ultrasonic signals with the detector of the probe;

determining a velocity of the third ultrasonic signals through the third ball joint;

utilizing the velocities of the first and the second ultrasonic signals through the first and the second ball joints, the known hardness of the first bail joint and the known hardness of the second ball joint, and the velocity of the third ultrasonic signals to determine a hardness of the third ball joint; and either accepting or rejecting the third ball joint based on the determined hardness thereof.

10. The method of determining the hardness of a ball joint according to claim 9, further comprising:

ensuring frequencies of the first, the second and the third ultrasonic signals are the same;

considering overall longitudinal lengths of the first, the second and the third ball joints when determining the respective hardness of the first, the second and the third ball joints;

establishing a minimum threshold velocity from the velocities of the first ultrasonic signals and the velocities of the second ultrasonic signals, and the known hardness of the first ball joint and the known hardness of the second ball join; and ascertaining the hardness of the third bail joint based on the velocity of the third ultrasonic signals passing through the third ball joint.

11. The method of determining the hardness of a ball joint according to claim 9, further comprising:

heat treating the third ball joint in a manufacturing process to harden an outer surface of the third ball joint; and determining adequacy of the heat treatment of the third bail joint based on the determined hardness of the third ball joint.

12. The method of determining the hardness of the component to be tested according to claim 1, further comprising:

qualifying the first end surface of the component to be tested to ensure alignment of a longitudinal axis of the probe with the longitudinal axis of the component to be tested.

13. The method of determining the hardness of the component to be tested according to claim 1, further comprising:

machining the first end surface of the component to be tested to ensure that the first end surface is flat and perpendicular to the longitudinal axis of the component to be tested, and facilitate proper alignment of the probe and the component to be tested; and positioning a flat end face of the probe relative to the component such that the end face of the probe is parallel to and abuts the first end surface of the component.

* * * * *